United States Patent [19]

Renz et al.

[11] Patent Number: 4,955,740
[45] Date of Patent: Sep. 11, 1990

[54] WELDED JOINT BETWEEN PLASTIC PARTS

[75] Inventors: Rainer Renz, Stuttgart; Karl-Heinz Ilzhoefer, Reichenbach/Fils, both of Fed. Rep. of Germany

[73] Assignee: Daimler Benz Aktiengesellschaft, Stuttgart, Fed. Rep. of Germany

[21] Appl. No.: 140,588

[22] Filed: Jan. 4, 1988

[30] Foreign Application Priority Data

Jan. 9, 1987 [DE] Fed. Rep. of Germany ....... 3700465

[51] Int. Cl.$^5$ ............................ B25G 3/00; F16B 1/00
[52] U.S. Cl. ...................................... 403/27; 403/270; 156/276
[58] Field of Search .................. 403/270, 27; 156/276, 156/73.4, 272.4

[56] References Cited

U.S. PATENT DOCUMENTS 3,461,014  8/1969  James ............................... 156/272.4
3,574,031  4/1971  Heller, Jr. et al. ............. 156/276 X Primary Examiner—Andrew V. Kundrat
Attorney, Agent, or Firm—Evenson, Wands, Edwards, Lenahan & McKeown

[57] ABSTRACT

The invention relates to a welded joint between plastic parts, the welding quality of which can be checked in a non-destructive way. In particular, a coating of an X-ray contrast medium, of sharply set-off contour and of specific outline shape, is introduced, before welding, in the region of the welding gap. The coating is narrower or smaller than the zone to be welded. It can be a strip of specific width or a pattern comprising recurring contour parts. The coating can be printed on or take the form of an inserted auxiliary film. Coloring pigments based on heavy metal, metal powder, rock dust, powdered glass or ceramic powder come under consideration as X-ray contrast media.

29 Claims, 1 Drawing Sheet

WELDED JOINT BETWEEN PLASTIC PARTS

BACKGROUND AND SUMMARY OF THE INVENTION

The invention relates to a welded joint between plastic parts, such as are generally known in the plastic-processing industry for articles made of thermoplastics.

Where welded joints subjected to high loads are concerned, it is often desirable to check the strength of these. Mechanical processes for checking welded joints have a destructive effect, and in sampling which is approximately uniform in statistical terms this results in the destruction of many, sometimes very expensive workpieces.

An object of the invention, is to make a welded joint between plastic parts, in such a way that it can be checked for perfect welding quality reliably and in a non-destructive way.

According to the invention, this object is achieved by means of providing a coating of X-ray contrast medium with a sharp outline to one of the parts being welded. Because an X-ray contrast medium of sharp outer contour is introduced into the welding gap before the parts are joined together, it is possible, after the welded joint has been made, to ascertain whether the outer contour of the X-ray contrast medium has run within the welding material, this pointing to a good welding quality, or whether the edge contour of the coating of X-ray contrast medium is more or less sharply set-off, as before; in the latter case, this would point to poor running of the material within the welding gap and therefore to a poor welding quality.

Preferred embodiments of the invention use a film strip to carry the X-ray contrast medium. In certain preferred embodiments the film strip has saw tooth edge portions. The preferred embodiment use various X-ray contrast medium material to facilitate economical and efficient production techniques.

Other objects, advantages and novel features of the present invention will become apparent from the following detailed description of the invention when considered in conjunction with the accompanying drawings.

DETAILED DESCRIPTION OF THE DRAWING

Figure 1:
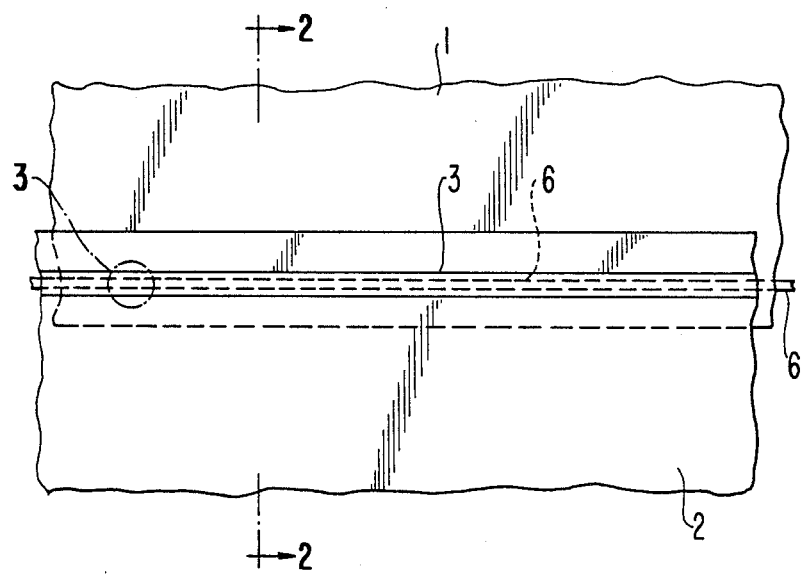
FIG. 1 is a partial schematic top view of a weld seam for joining two plastic parts constructed according to a preferred embodiment, of the invention.
Figure 2:
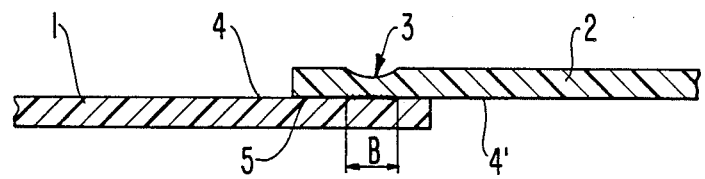
FIG. 2 shows a cross-section through the weld seam according to FIG. 1 taken along the sectional line II—II.

FIGS. 1 and 2 show, in cut-out form, a first plastic part 1 and a second plastic part 2 which are welded to one another via a linear weld seam 3. The two plastic parts are in contact with one another by means of the mutually confronting surfaces 4 and 4' and form a welding gap 5. The plastic parts 1 and 2 to be welded together preferably consist of fibre-reinforced polypropylene, especially glass-fibre-reinforced polypropylene, for example with a proportion of glass fibres of 40 percent. The weld seam 3 between the two plastic parts 1 and 2 is made by heating the plastic in the region of the weld seam up to or above the melting temperature of the plastic by means of suitable processes, with pressure being exerted on the two plastic parts. Various heating processes are known for this purpose, but these need not be discussed in detail in this connection. The only examples which need to be mentioned are ultrasonic heating or heating in an electrostatic alternating field or heating by means of normal thermal conduction.

Since heating is to take place at high speed, the necessary welding temperature will not always be reached, either because there has not been sufficient time for this or because there are defects in the welding appliances and/or in the welding material. Where important welds are concerned, it is desirable to check their quality in a non-destructive way. To make this possible, according to the invention a coating of an X-ray contrast medium is introduced into the welding gap before the welding operation, the coating having a sharply set-off outer contour with a specific outline shape.

In the exemplary embodiment illustrated in FIG. 1. to 3, the coating with the X-raY contrast medium is contained on a jointly weldable auxiliary film inserted into the welding gap and taking the form of a film strip 6. Instead of this film strip 6, the X-ray contrast medium could also be printed directly onto one of the plastic parts to be welded together, as an appropriate line or as an appropriate linear pattern, according to other preferred embodiments of the invention. Even if the X-ray contrast medium is introduced in the form of an auxiliary film, it can be printed onto the auxiliary film; preferably, however, an auxiliary film strip provided with X-ray contrast medium in its mass will be used for the sake of simplicity. The film strip or, if the workpiece or the film strip is printed with X-ray contrast medium, the printed-on pattern have, in the non-welded state, a sharply set-off contour of specific shape.

Figure 3:
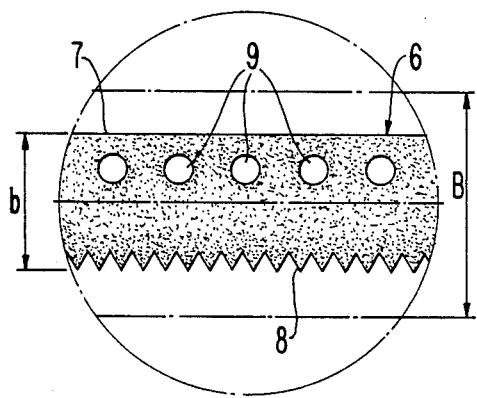
FIG. 3 shows an enlarged X-ray picture through the weld seam according to FIG. 1 at the point III, different alternative designs being shown in the lower and the upper half, but in the state before welding is carried out.

FIG. 3 shows various exemplary embodiments of such specific contour shapes in the non-welded state. The edge of the coating can be limited by a straight line saw-tooth edge limitation on 8 or by a hole pattern 9 consisting of holes which are round or of another shape, for example, square or star-shaped. It is necessary to ensure, at all events, that the pattern width (the dimension b) of the X-ray contrast medium, before the latter is introduced into the weld seam, is narrower than the welding width B of the weld seam 3. The pattern width can be, for example, the distance between the two opposite limiting edges of the film strip or the distance between two parallel rows of holes on the film strip.

There are various possibilities for forming the X-ray contrast medium. It can be stated, in principle, that particles having a higher density than the basic material, when irradiated with weak X-rays, are contrasted relative to the basic material, in particular thermoplastics. The higher the density of the individual particles of the X-ray contrast medium, the sharper the contrast. For example, coloring pigments based on heavy metals already have a higher specific density than plastic, so that these would be suitable as X-ray contrast media. It is therefore contemplated to use a narrow film strip dyed in its mass, dyes with coloring pigments based on heavy metals being used for dying this. Dyes of this type are also employed in the dying of plastics. Another arrangement for forming the X-ray contrast medium is to use rock dust, powdered glass or ceramic powder. This arrangement can also be adopted in addition to the use of coloring pigments based on heavy metals. Another possibility for forming the X-ray contrast medium, which can be adopted alternatively or in addition, is to use fine metal powder, especially iron powder.

Figure 4:
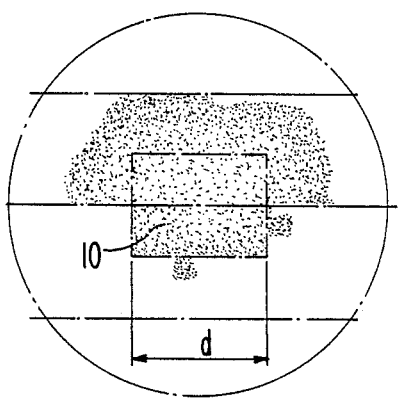
FIG. 4 shows a further practical example of an X-ray picture, the coating with the X-ray contrast medium being introduced as a small rectangle, the upper half of the picture representing a good welding quality and the lower half of the picture a poor welding quality.

As mentioned, FIG. 3 shows only exemplary embodiments of coating contours in the still non-welded stated, essentially a strip-shaped coating of X-ray contrast medium having been introduced along a linear weld seam. FIG. 4, by the example of an individual welding spot and, correspondingly, of an inserted small rectangular stamping 10 of a film containing the X-ray contrast medium, shows, in the upper half of the picture, how the contour of the X-ray contrast medium appears after a perfect weld has been made and, in the lower half of the picture how the edge contour of the X-ray contrast medium appears after a poor weld. It may also be mentioned once more, at this juncture, that the stamping sized is less than the width B of the weld seam. Of course, even where a continuous linear weld seam is concerned, individual stampings 10 can be scattered like confetti onto the weld seam in close succession.

As shown in the upper half of FIG. 4, the X-ray contrast medium is deformed irregularly and to a very great extent in relation to the original stamping contour represented by dot-and-dash lines, which points to the fact that the basic material has run to a pronounced degree in the region of the weld and has melted into itself. This indicated an intimate material bond within the weld, that is to say a good welded joint. The edge contour, as shown in the lower half of the picture of FIG. 4, tells a different story. The original contour of the stamping 10 is still largely perserved in the X-ray picture; only at two small locations on the periphery has the contour of the X-ray contrast medium run somewhat, this pointing to only very small points where there is a material bond and which cannot be subjected to load. Welds showing such a picture or a similar picture of the X-ray contrast medium indicate poor welding.

It should not be overlooked, here, that there have recently also been processes for the electromagnetic heating of the plastic to be welded together, a plastic strip containing iron powder being introduced along the line of the weld seam before welding. By means of induction coils following the line of the weld seam, the iron particles are heated inductively and thus heat not only the inserted film strip, but also the adjacent basic material. At the same time or thereafter, the parts are pressed together, being joined to one another. Admittedly, in this heating process for plastic welding, it is a process-related pre-condition that an agent also functioning as an X-ray contrast medium, in particular iron powder, is introduced into the welding gap before welding. However, even in the light of such a welding process, the present invention represents an appropriate technical teaching for the non-destructive checking of a weld seam, because a specific hole pattern or a specific edge contour is provided on the iron-powder coating to be introduced, which keeps within the welding width B, so that it remains possible, under all circumstances, to check in the X-ray picture whether intimate running of the inserted coating has taken place or not. The invention can also be used irrespective of electromagnetic heating of the welding gap; an appropriate insertion of an X-ray contrast medium with other types of heating for making a plastic weld is expedient for the purpose of checking it in a non-destructive way.

Although the present invention has been described and illustrated in detail, it is to be clearly understood that the same is by way of illustration and example only, and is not to be taken by way of limitation. The spirit and scope of the present invention are to be limited only by the terms of the appended claims.

What is claimed:

1. Welded joint between plastic parts, wherein at least one of the plastic parts to be welded together is provided with a jointly weldable coating of an X-ray contrast medium containing coloring pigments based on heavy metals, and having a sharply set-off outer contour and a specific outline shape, said coating being disposed in the region of the surface in contact with the other plastic part at the welded joint.

2. Welded joint according to claim 1, wherein the coating is printed directly onto one of the plastic parts to be welded together.

3. Welded joint according to claim 1, wherein the coating is contained on a jointly weldable auxiliary film inserted into the welding gap.

4. Welded joint according to claim 1, wherein the coating is printed onto the auxiliary film.

5. Welded joint according to claim 3, wherein the coating is formed by the margin of the auxiliary film which is provided with X-ray contrast medium in its mass.

6. Welded joint according to claim 5, wherein the auxiliary film is in the form of a film strip following the line of the weld seam.

7. Welded joint according to claim 6, wherein the film strip is provided with at least one of an edge contour of specific shape and a hole pattern of specific shape.

8. Welded joint according to claim 4, wherein the auxiliary film is in the form of at least one stamping or strip portion, the diameter of which is less than the weld width.

9. Welded joint according to claim 1, wherein the plastic parts to be welded together consist of fiber-reinforced polypropylene.

10. Welded joint according to claim 1, wherein the plastic parts to be welded together consist of fibre-reinforced polypropylene.

11. Welded joint according to claim 3, wherein the plastic parts to be welded together consist of fiber-reinforced polypropylene.

12. Welded joint according to claim 3, wherein the X-ray contrast medium contains at least one of rock dust, powdered glass and ceramic powder.

13. Welded joint according to claim 1, wherein said coating is narrower than the portion of the joint to be welded.

14. Welded joint between plastic parts, wherein at least one of the plastic parts to be welded together is provided with a jointly weldable coating of an X-ray contrast medium containing at least one of rock dust, powdered glass and ceramic power and having a sharply set-off outer contour and a specific outline shape, said coating being disposed in the region of the surface in contact with the other plastic part at the welded joint.

15. Welded joint according to claim 14, wherein the coating is printed directly onto one of the plastic parts to be welded together.

16. Welded joint according to claim 14, wherein the coating is contained on a jointly weldable auxiliary film inserted into the welding gap.

17. Welded joint according to claim 16, wherein the coating is printed onto the auxiliary film.

18. Welded joint according to claim 16, wherein the coating is formed by the margin of the auxiliary film which is provided with X-ray contrast medium in its mass.

19. Welded joint according to claim 18, wherein the auxiliary film is in the form of a film strip following the line 20. Welded joint according to claim 19, wherein the film strip is provided with at least one of an edge contour of a specific shape and a hole pattern of specific shape.

21. Welded joint according to claim 17, wherein the auxiliary film is in the form of at least one stamping or strip portion, a diameter of which is less than the weld width.

22. Welded joint according to claim 14, wherein the X-ray contrast medium contains coloring pigments based on heavy metals.

23. Welded joint according to claim 14, wherein the plastic parts to be welded together consist of fiber-reinforced polypropylene.

24. Welded joint according to claim 14, wherein the plastic parts to be welded together consist of fiber-reinforced polypropylene.

25. Welded joint according to claim 16, wherein the plastic parts to be welded together consist of fiber-reinforced polypropylene.

26. Welded joint according to claim 16, wherein the X-ray contrast medium contains coloring pigments based on heavy metals.

27. Welded joint according to claim 14, wherein said coating is narrower than the portion of the joint to be welded.

28. A method of forming a welded joint between plastic parts, comprising:
applying a weldable coating of an X-ray contrast medium containing at least one of rock dust, powdered glass and ceramic powder and having a sharply set-off outer contour and a specific outline shape to a plastic part to be welded; and
welding the plastic part to another plastic part along the area of the coating.

29. A method of forming a welded joint between plastic parts, comprising:
applying a weldable coating of an X-ray contrast medium containing coloring pigments based on heavy metals and having a sharply set-off outer contour and a specific outline shape to a plastic part to be welded; and
welding the plastic part to another plastic part along the area of the coating.

* * * * *